(12) United States Patent
Bonnet

(10) Patent No.: US 11,433,239 B2
(45) Date of Patent: Sep. 6, 2022

(54) ACTIVE IMPLANTABLE MEDICAL DEVICE FOR THE TREATMENT OF HEART FAILURE WITH VAGUS NERVE STIMULATION

(71) Applicant: SORIN CRM SAS, Clamart (FR)

(72) Inventor: Jean-Luc Bonnet, Massy (FR)

(73) Assignee: Sorin CRM SAS, Clamart (FR)

( * ) Notice: Subject to any disclaimer, the term of this patent is extended or adjusted under 35 U.S.C. 154(b) by 388 days.

(21) Appl. No.: 16/396,380

(22) Filed: Apr. 26, 2019

(65) Prior Publication Data

US 2019/0247663 A1 Aug. 15, 2019

Related U.S. Application Data

(62) Division of application No. 14/256,661, filed on Apr. 18, 2014, now Pat. No. 10,300,280.

(30) Foreign Application Priority Data

Apr. 19, 2013 (FR) ...................................... 1353582

(51) Int. Cl.
*A61N 1/36* (2006.01)
*A61N 1/362* (2006.01)
(Continued)

(52) U.S. Cl.
CPC ...... *A61N 1/36114* (2013.01); *A61N 1/36053* (2013.01); *A61N 1/36139* (2013.01);
(Continued)

(58) Field of Classification Search
CPC ............ A61N 1/36114; A61N 1/36053; A61N 1/36139; A61N 1/3627; A61N 1/36542; A61N 1/36535; A61B 5/1118
See application file for complete search history.

(56) References Cited

U.S. PATENT DOCUMENTS 5,514,162 A * 5/1996 Bornzin ............. A61N 1/36542
607/19
5,793,642 A * 8/1998 Frisch .................. G01R 31/316
703/4
(Continued)

FOREIGN PATENT DOCUMENTS

WO  WO-2005/102449 A1  11/2005

OTHER PUBLICATIONS

Preliminary Search Report for French Patent Application No. 1353582, dated Jul. 10, 2013, 2 pages.

*Primary Examiner* — Michael W Kahelin
*Assistant Examiner* — Pamela M. Bays
(74) *Attorney, Agent, or Firm* — Foley & Lardner LLP

(57) ABSTRACT

An active implantable medical device includes a VNS pulse bursts generator for stimulation of the vagus nerve according to several selectable configurations. The device may further include a sensor of the current activity level of the patient. The generator is controlled on the activity signal via a classifier determining the class of the current level of activity among a plurality of classes of activity. A controller selects a configuration of VNS therapy depending on the class of activity thus determined. Limits of the activity classes are dynamically changeable by a calibration module that conducts a historical analysis of the successive current activity levels over a predetermined analysis period. The calibration module can prepare a histogram of the historical analysis, and can define the limits of the activity classes depending on the outcome of the historical analysis and the histogram.

8 Claims, 3 Drawing Sheets

(51) Int. Cl.
  *A61B 5/11*      (2006.01)
  *A61N 1/365*     (2006.01)

(52) U.S. Cl.
  CPC ......... *A61B 5/1118* (2013.01); *A61N 1/3627* (2013.01); *A61N 1/36535* (2013.01); *A61N 1/36542* (2013.01)

(56) References Cited

U.S. PATENT DOCUMENTS

| | | | |
|---|---|---|---|
| 6,128,534 A * | 10/2000 | Park | A61N 1/36542 607/17 |
| 6,572,557 B2 | 6/2003 | Tchou et al. | |
| 7,801,603 B2 * | 9/2010 | Westlund | A61N 1/36053 607/2 |
| 2006/0095081 A1 * | 5/2006 | Zhou | A61N 1/36114 607/2 |
| 2007/0021678 A1 | 1/2007 | Beck et al. | |
| 2010/0010338 A1 | 1/2010 | Van Dam et al. | |
| 2012/0095530 A1 | 4/2012 | Chavan et al. | |
| 2016/0136428 A1 | 5/2016 | Bonnet et al. | |

\* cited by examiner

ACTIVE IMPLANTABLE MEDICAL DEVICE FOR THE TREATMENT OF HEART FAILURE WITH VAGUS NERVE STIMULATION

CROSS-REFERENCE TO RELATED PATENT APPLICATIONS

This application is a divisional from U.S. patent application Ser. No. 14/256,661, entitled "ACTIVE IMPLANTABLE MEDICAL DEVICE FOR THE TREATMENT OF HEART FAILURE WITH VAGUS NERVE STIMULATION," filed Apr. 18, 2014, now issued as U.S. Pat. No. 10,300,280, which claims the benefit of and priority to French Patent Application No. 1353582, filed Apr. 19, 2013, each of which is hereby incorporated by reference herein in its entirety.

BACKGROUND

The invention relates to "active implantable medical devices" as defined by Directive 90/385/EEC of 20 Jun. 1990 of the Council of the European Communities. This invention more particularly relates to implants for delivering therapies of stimulation of the vagus nerve, called VNS therapies (Vagus Nerve Stimulation). It more particularly relates to the use of such therapies in patients at risk of heart failure.

Stimulation of the vagus nerve affects cardiovascular functions by reducing the heart rate and the myocardial contractility with decreased length of diastole. Such effects can help reduce the development of cardiac remodeling which may lead to heart failure.

In general, patients with heart failure have a reduced level of physical activity. Often a maximum effort level is correlated with the severity of heart disease. Although physical activity is recognized as a therapy to improve heart function, these patients struggle to produce physical activity due to the reduction in their heart function, so they can only accomplish bits of exercise. Due to the reduction in heart rate and of the myocardial contractility that results from VNS therapy, a VNS therapy may actually be an aggravating factor in exercise tolerance (e.g., because it may reduce the responsiveness of the heart to current activity). Indeed, even in view of physical effort, VNS stimulation may prevents the heart rate from accelerating, neutralizing the beneficial effect of increased physical activity.

To overcome this difficulty it has been suggested, for example, in U.S. 2012/0095530 A1, to adapt the VNS therapy based on the activity level of the patient, which shall be assessed by a suitable sensor such as an accelerometer integrated in the case of the implantable stimulation pulse generator. The sensor signal is compared with a set of predefined thresholds and the VNS stimulation parameters, primarily the stimulation energy, are selectively adjusted according to the crossed thresholds (e.g., to tailor the therapy so that heart rate can increase with the effort be expressed). In this device, the modulation of the VNS therapy is defined in terms of absolute criteria, namely predefined thresholds. However, the level of activity can vary from a patient to another, and also over time for the same patient, depending on the medium and/or long-term evolution (e.g. from one day to another and/or over a period of several days or weeks) of the disease which the patient suffers from. Changes might be an improvement in condition or a worsening.

SUMMARY

The object of the invention is to overcome the above difficulty by proposing a device equipped with a tracking of the VNS stimulation generator specifically operating for each patient through an automatic calibration of this tracking, with further opportunity to repeat this calibration at regular intervals (e.g. daily) to monitor the condition of the patient in the medium and long term. To this end, the invention discloses a medical device for the treatment of heart failure with VNS stimulation. The device includes a generator that produces pulse bursts according to several configurations of selectable different VNS therapies. The device further includes a sensor adapted to generate an activity signal based on the current level of activity of the patient. The device further includes a tracking module that includes a classifier configured to determine to which class the current level of activity of the patient belongs to from a plurality of activity classes. The classes may be defined by varying boundaries of activity level. The device further includes a controller adapted to select a respective VNS therapy configuration in accordance with the class of activity determined by the classifier.

Advantageously, the boundaries that define the activity classes are dynamically modifiable boundaries. The device includes a calibration module for the classifier. The calibration module can use historical analysis of the successive levels of current activity of the patient taken during a predetermined analysis period. The calibration module can thereafter define boundaries of the activity classes based on the results of said historical analysis.

The device can include a module for updating the classifier. Such a module can, for example, repeatedly activate (e.g., at regular intervals) the calibration module of the classifier. The calibration module of the classifier can include a sampling module for the successive current activity levels of the patient during the analysis period, a module for constructing a histogram of the sampled activity levels, and a module for partitioning the histogram into the plurality of activity classes.

Partitioning the histogram may include defining the boundaries between successive classes so that the cumulative sum of the sampled levels in each class is a predetermined fraction, preferably identical for all classes, of the cumulative sum of the sampled levels.

In a particular implementation, the calibration module of the classifier determines a minimum value and a maximum value of activity levels sampled during the analysis period, the partitioning of the histogram can be conducted between these minimum and maximum values.

The calibration module may also determine a nominal value of rest and a nominal value during exercise based on activity levels sampled during the analysis period. The partitioning can be conducted by partitioning the histogram between these values of rest and exercise. The nominal value of rest, respectively of exercise, may in particular be defined as a function of a predetermined percentage of the cumulative sum of the all class sampled levels. The sampling module can find an average activity level during each respective sampling period.

According to another embodiment, an active implantable medical device includes a VNS pulse bursts generator for stimulation of the vagus nerve according to several selectable configurations. The device may further include a sensor of the current activity level (A) of the patient. The generator is controlled on the activity signal via a classifier determining the of class the current level of activity among a plurality of classes of activity (T1-T4). A controller selects a configuration of VNS therapy depending on the class of activity thus determined. Limits of the activity classes are dynamically changeable by a calibration module that conducts a historical analysis of the successive current activity levels over a predetermined analysis period. The calibration module can prepare a histogram (C) of the historical analysis, and can define the limits of the activity classes (T1 . . . T4) depending on the outcome of the historical analysis and the histogram.

DETAILED DESCRIPTION

Such a pacemaker includes a programmable microprocessor provided with circuits for processing and delivering stimulation pulses to implantable electrodes. It is possible to transmit to it (e.g., via telemetry electronics) software that is stored in memory and executed to implement the functions of the invention that are described below. The methods and modules of the present specification may be implemented by appropriate programming of the control software of a VNS stimulator. In particular, the methods may be implemented by software (e.g., by appropriate computer code algorithms stored in memory and executed by a microcontroller or a digital signal processor). For the sake of clarity, the various processing applied will be broken down and diagrammed by a number of different functional blocks in the form of interconnected circuits, however this representation is only illustrative. Other embodiments may fall within the scope of the appended claims.

Figure 1:
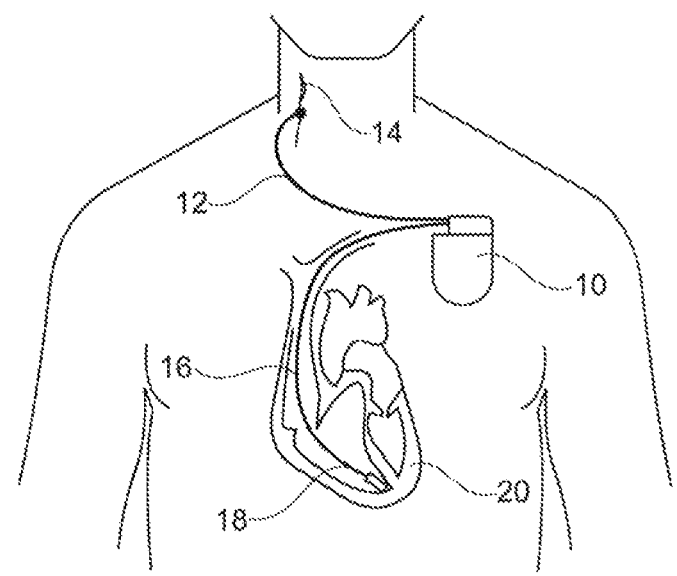
FIG. 1 is an illustration providing an overview of the device of the invention, showing the generator, leads, the myocardium and the vagus nerve.

In FIG. 1, the reference 10 designates the housing of an implantable generator for vagus nerve stimulation. The stimulation is delivered by a lead 12 bearing at its distal end an electrode implanted on the vagus nerve 14. The generator 10 applies produced pulse trains that are used to stimulate the nerve. To allow delivery of VNS pulses in synchronism with the heartbeat, the generator 10 also has a cardiac lead 16 with an electrode 18 provided at its distal end for collecting the electrical activity of the myocardium 20. For example, the cardiac lead 16 and electrode 18 may be used to collect endocardial electrogram signals, which are then used to drive the generator 10. The goal of such synchronization may be to deliver stimulation pulses as a function of the heart rate and at the most appropriate moment of the cardiac depolarization wave.

Figure 2:
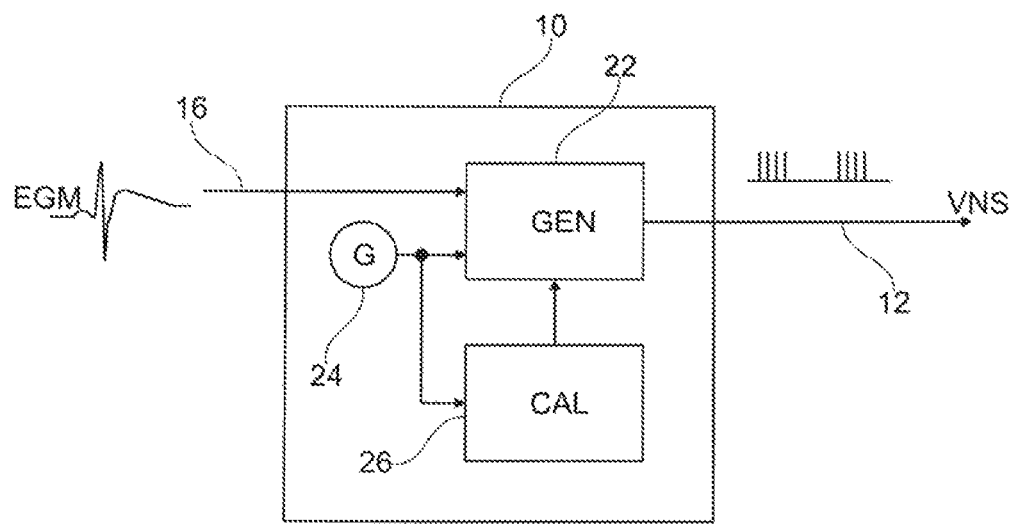
FIG. 2 is a schematic block corresponding to the generator of the device.

FIG. 2 schematically illustrates the main functions implemented within the housing 10 as part of the invention. This housing includes a pulse generator 22 of VNS delivered to the vagus nerve via the lead 12 at the output. Regarding inputs, the generator 22 is controlled, firstly, by the EGM electrogram signal delivered by the lead 16 and, secondly, by an activity signal delivered by a sensor 24.

The sensor 24 may be a motion sensor such as an accelerometer sensor, or "G sensor". Other types of sensors may be used, for example (as will be described below in connection with FIGS. 4 to 6) a physiological sensor such as a minute ventilation sensor or "MV sensor", providing an indication of the patient activity level according to metabolic needs notably measured from the rhythm and from the respiratory volume.

The activity sensor 24 is used for controlling or modulating the VNS therapy according to the detected current level of activity, for example by selection between several energy levels of the VNS stimulation pulses. This may include, for some patients, stimulating with decreasing energy gradually as the activity increases, so as not to prevent the heart rate from accelerating due to the effort produced by the patient.

For other heart failure patients who have poorly controlled spontaneous heart rate despite the treatment with beta-blockers, the therapeutic goal may be, conversely, to decrease heart rate during exercise, so to increase the energy level of the VNS therapy with activity.

This modulation of the VNS therapy results from the comparison of the level of activity measured by the sensor 24 to a series of successive thresholds, these thresholds corresponding to limits of a set of "classes" of the patient activity. Advantageously provided by the present invention, these different classes and their limits are no longer defined in a fixed and undifferentiated manner, but so as to better adapt to suit the patient and to be dynamically changeable over time. For this purpose, the device includes a calibration circuit 26 (i.e., a calibration module comprising executable computer code stored in memory) to establish and recalculate the thresholds of the different classes of activity. The generator 22 can use these thresholds to select the appropriate VNS therapy.

This calibration circuit 26 may operates from activity measurements delivered by the sensor 24 according to systems and methods as described below. Successive samples of the patient's activity are collected over a predetermined time (e.g., over the last 24 hours). Each sample may be an average (or some other aggregate) of the level of activity measured by the sensor over a period of a few seconds, so as to smooth the instantaneous variations of the accelerometric signal. In other embodiments, a median or a non-smoothed signal are used.

Figure 3:
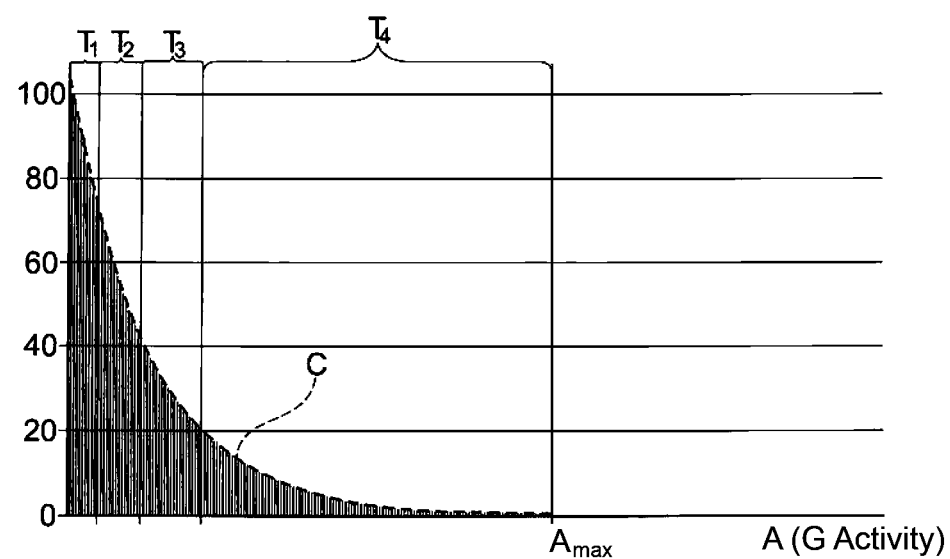
FIG. 3 is a 24-hour histogram of patient activity detected by an accelerometer sensor. This Figure illustrates the partitioning of this histogram into four classes corresponding to four different configurations of VNS therapy.

The calibration circuit 26 then sets up a histogram of the set of values thus measured and stored for 24 hours. An example of this histogram is illustrated in FIG. 3, with the A activity level corresponding to each sample value in abscissa, and the number of occurrences of each of these values in ordinate.

The activity A varies between zero level (immobility of the patient, for example during periods of rest or sleep) and a maximum level of activity Amax, which can vary significantly from one day to another depending on the maximal exercise produced by the patient during the day in question. The envelope of this histogram is a curve C related to a specific activity profile, specific to the patient and to the considered period of 24 hours.

The calibration circuit then partitions the histogram into a plurality of classes or slots, for example four slots T1-T4, each corresponding to a different configuration of VNS therapy that may be selected by the generator 22 (e.g., therapies for each activity level differing in their stimulation energy level, which may gradually decrease, for example, when the current activity of the patient increases).

The partition may be performed according to a predetermined relation. For example, in the illustrated example, the successive classes T1-T4 are defined so that the cumulative sum of sampled levels in each class is a predetermined fraction, e.g. an identical fraction of 25%, of the cumulated sum of sampled levels of all classes. In other words, the boundaries between the successive classes T1-T4 are selected so that the area under the curve C is the same for each of the classes, and equal to 25% of the total area under the curve C.

The thresholds defining the boundaries between the classes T1-T4 thus determined are stored by the generator 22, which can then select a particular VNS therapy depending on the current level of activity of the patient.

Calibration as described above is preferably repeated at regular intervals, for example every 24 hours or every 48 hours, in order to incorporate a possible evolution of the condition of the patient, positive or negative.

Other modes of dynamic definition of the different classes can be considered. Thus, as illustrated in FIGS. 4 to 6, in the case wherein a physiological sensor of the minute ventilation MV type is used to measure the activity, it is necessary to previously determine the activity values at rest $A_{rest}$ and maximal exercise activity $A_{effort}$.

Figure 4:
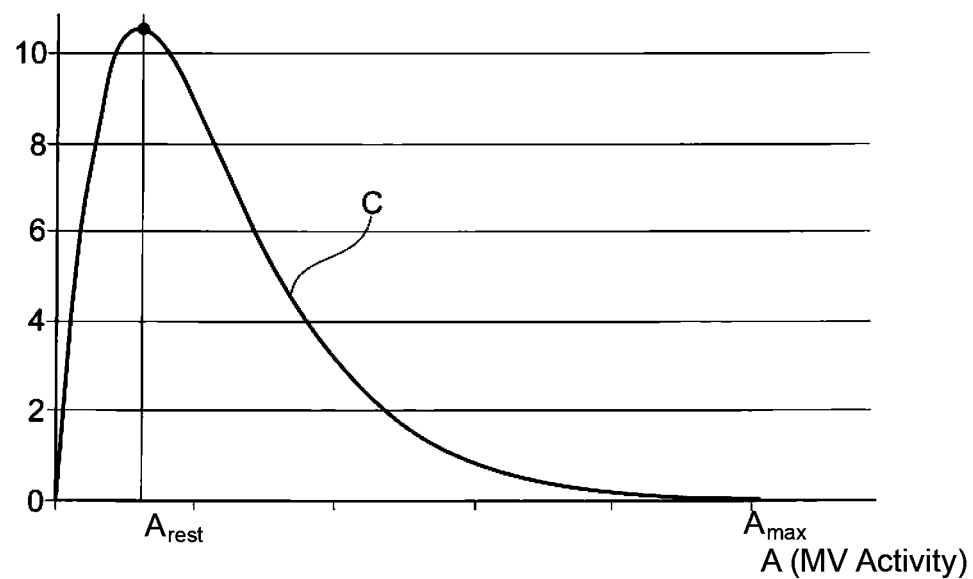
FIG. 4 shows the profile of a histogram established over 24 hours of the mean values of patient activity collected using a physiological minute ventilation sensor.

Indeed, as can be seen in FIG. 4, the envelope curve C of the histogram obtained from the sampled measurements produced by the MV sensor (homologous histogram to that obtained with a G sensor in FIG. 3) does not vary monotonically but has a peak corresponding to the activity at rest.

Figure 5:
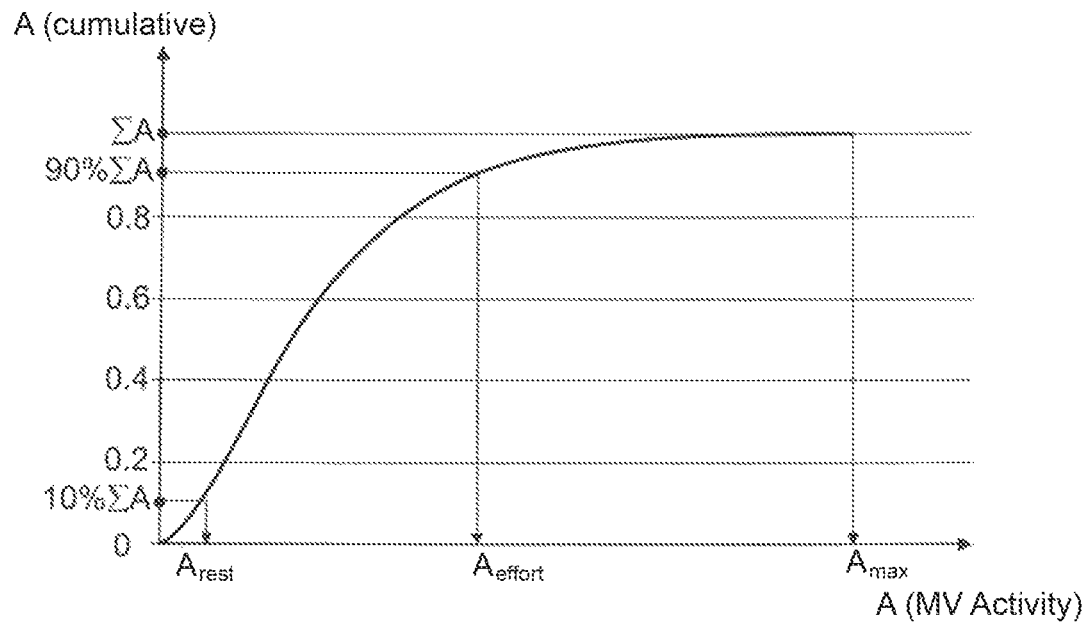
FIG. 5 is derived from the histogram in FIG. 4 after accumulation of the collected values and defines definition of activity levels of rest and of exercise.
Figure 6:
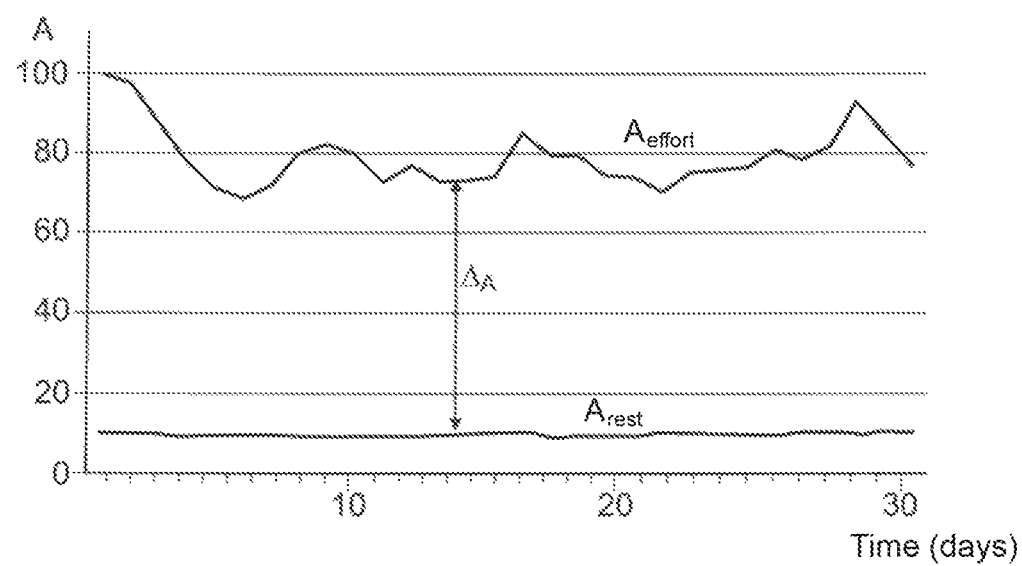
FIG. 6 is a diagram showing the long-term evolution of the activity levels of rest and of exercise as daily determined as illustrated in FIG. 5.

To determine the position of this peak, the calibration circuit calculates a cumulated sum of the values of the histogram, giving a profile such as that illustrated in FIG. 5, with a cumulated value ranging between zero and EA (total of all sampled values of the histogram).

The level of activity at rest $A_{rest}$ may be defined, for example, as corresponding to 10% of $\Sigma A$ and the activity level at effort $A_{effort}$ as that corresponding to 90% of $\Sigma A$. Partitioning successive classes is then operated in the manner described above, between the two extreme ends of $A_{rest}$ and $A_{effort}$.

This technique may advantageously take into account the highly variable dynamics AA from one day to another between $A_{rest}$ and $A_{effort}$ as shown in FIG. 6, which represents on a period of 30 days the evolution of the levels of activity $A_{effort}$ and at rest $A_{rest}$ as daily determined in the manner described above.

What is claimed is:

1. An active implantable medical device, comprising:
    a pulse generator for stimulation of a vagus nerve;
    an interface configured to receive an indication of activity level;
    a control circuit coupled to the interface and the pulse generator, the control circuit configured to determine a class of a current level of activity among a plurality of classes of activity and selects a configuration of pulse therapy for the pulse generator depending on the determined class of activity;
    wherein the class of the current level of activity is determined by comparing the current level of activity to a plurality of thresholds of activity that define the plurality of classes of activity;
    wherein the control circuit is further configured to dynamically change the plurality of thresholds of activity that define the plurality of classes of activity based on a historical analysis of successive current activity levels over an analysis period;
    wherein the pulse generator delivers the pulse therapy to the vagus nerve based on the selected configuration.

2. The active implantable medical device of claim 1, wherein the control circuit is further configured to prepare a histogram of the historical analysis and define the plurality of thresholds of the plurality of classes of activity depending on an outcome of the historical analysis and the histogram.

3. The active implantable medical device of claim 2, wherein the control circuit is further configured to re-partition the prepared histogram into the plurality of classes of activity based on recent activity history to generate the plurality of thresholds.

4. The active implantable medical device of claim 3, wherein the re-partitioning of the histogram comprises defining limits between successive activity classes so that a cumulative sum of sampled activity levels in each class is a predetermined fraction of a cumulative sum of sampled activity levels of all classes.

5. The active implantable medical device of claim 4, wherein said predetermined fraction is a fraction identical for all classes of activity.

6. The active implantable medical device of claim 3, wherein the control circuit is further configured to determine a minimum value and a maximum value of said activity levels sampled during the analysis period and partition the histogram between said minimum and maximum values.

7. The active implantable medical device of claim 3, wherein the control circuit is further configured to determine a nominal value of rest and a nominal value of effort according to said activity levels sampled during the analysis period, and wherein the control circuit is further configured to partition the histogram between the determined nominal value of rest and nominal value of effort.

8. The active implantable medical device of claim 7, wherein the nominal value of rest and the nominal value of effort are defined based on a predetermined percentage of a cumulative sum of the sampled activity levels of all classes.

* * * * *